(12) United States Patent
Saito

(10) Patent No.: US 6,372,265 B2
(45) Date of Patent: Apr. 16, 2002

(54) ANTI-OXIDANT REDUCING SUBSTANCE AND METHOD OF PRODUCING THE SAME

(75) Inventor: Kahee Saito, Gunma (JP)

(73) Assignee: Yojogen Co., Ltd., Chiba (JP)

( * ) Notice: Subject to any disclaimer, the term of this patent is extended or adjusted under 35 U.S.C. 154(b) by 0 days.

(21) Appl. No.: 09/810,476

(22) Filed: Mar. 19, 2001

(30) Foreign Application Priority Data

Apr. 25, 2000 (JP) ........................................ 2000-123819

(51) Int. Cl.⁷ .......................... A01K 59/06; A61K 33/06
(52) U.S. Cl. ........................................ 424/682; 424/600
(58) Field of Search ................................ 424/682, 600

(56) References Cited

FOREIGN PATENT DOCUMENTS

| JP | 2-49747 | 2/1990 |
|---|---|---|
| JP | 11235192 | 8/1999 |
| JP | 11343234 | 12/1999 |

OTHER PUBLICATIONS

English Language Abstract of JP 2–49747.
English Language Abstract of JP 11–235192.
English Language Abstract of JP 11–343234.

*Primary Examiner*—Leon B. Lankford, Jr.
*Assistant Examiner*—Brett Ozga
(74) *Attorney, Agent, or Firm*—Greenblum & Bernstein P.L.C.

(57) ABSTRACT

The anti-oxidant substance according to the invention is obtained by adding calcium ion powder to a powdery curcuma. The calcium ion powder is obtained by adding calcium powder with ionic water and drying it and the anti-oxidant substance according to the invention has an excellent anti-oxidant effect and is capable of being safely ingested.

15 Claims, 1 Drawing Sheet

[Fig.1]
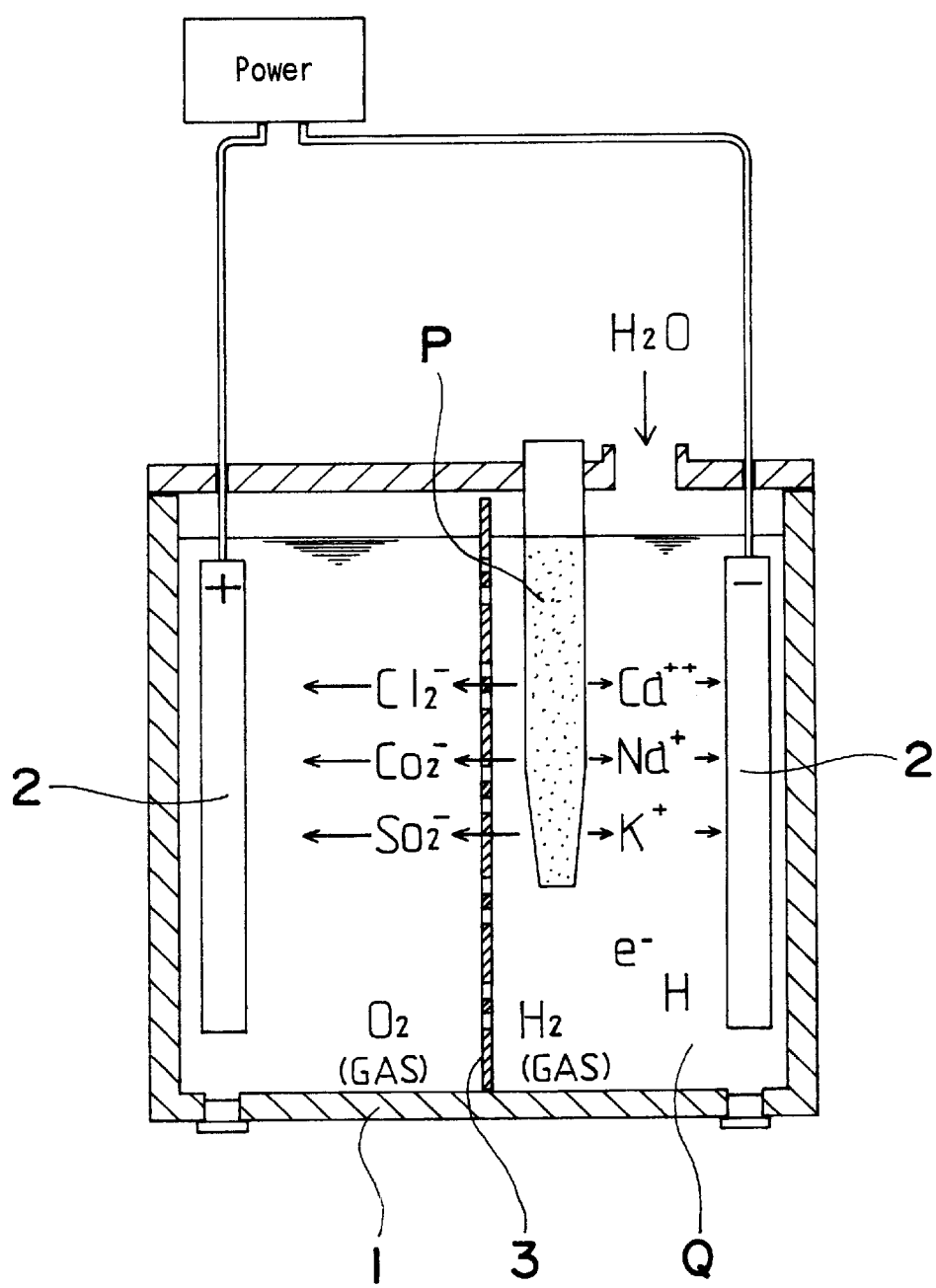

ANTI-OXIDANT REDUCING SUBSTANCE AND METHOD OF PRODUCING THE SAME

BACKGROUND OF THE INVENTION

1. Field of the Invention

This invention relates to a novel anti-oxidant reducing substance providing a high anti-oxidant effect by using water as a solvent and a method of producing the same.

2. Description of Related Art

It has been known that active oxygen in the body results in the occurrence of various disorders. Further, it is known from various studies and reports that curcumin has an anti-oxidant effect of removing or stabilizing the active oxygen and the like. And also, a curcuma (turmeric) used as a herb medicine, spices or the like contains a great amount of curcumin (curcuminoide).

The curcuma containing a great amount of curcumin is used as a Chinese traditional medicine. As a result of studies on and after "Research and Development for Prevention of Cancer Through Vegetable Foods" started by The National Cancer Laboratory in USA, there is reported a research result that a yellow coloring component of the curcuma, "curcumin" has effects of promoting secretion of bile in a liver to restrain various liver disorders and enhance an immune force in the body.

As a result of studies by a professor in Nagoya University (Japan), it has been confirmed that the curcumin having an anti-oxidant effect is slightly changed into a substance of tetrahydrocurcumin by binding with hydrogen in the body to develop a strong anti-oxidant effect. To this end, there have been proposed various methods of producing tetrahydrocurcumin having such a strong anti-oxidant effect. For example, JP-A-2-49747 discloses a method of producing tetrahydrocurcumin by dissolving curcumin extracted from curcuma into an organic solvent such as acetone or the like and subjecting the material to a reduction reaction with a metal catalyst such as Raney nickel catalyst or the like and a hydrogen gas. And also, JP-A-11-235192 discloses a method of producing tetrahydrocurcumins by acting mycelium and culture of a microorganism or a treating solution thereof on curcuma containing curcumin or the like.

However, these above conventional methods for the production of tetrahydrocurcumin have a problem that safety of the produced substance, quality of the produced substance itself and reliability of the production amount are lacking.

That is, the former production method uses metal catalyst, so that there is a problem in the edible and drinkable safety. And also, the reaction is carried out with gaseous hydrogen, so that there is still a problem in view of the gas control because there is caused a risk in the production.

On the other hand, the latter production method uses the mycelium and culture of the microorganism, so that if the environment conditions for growing the microorganism such as temperature, humidity, pH value and the like are changed somewhat, they immediately affect the quality of the substance to be produced. Therefore, it is very difficult to hold the quality of the produced substance and the production amount at constant level in the production method using the mycelium and culture of the microorganism.

Furthermore, tetrahydrocurcumin produced by these methods is a new tetrahydrocurcumin faded from a naturally originated yellow coloring matter. Since curcumin included in curcuma as a yellow coloring matter is proved to have an effect of controlling various liver disorders or enhancing an immune force in the body in addition to the anti-oxidant effect, however, it can be said that with such an extract of tetrahydrocurcumin it is difficult to expect a pharmaceutical effect more than the anti-oxidant effect. The inventor considers that the reason why the curcuma is used as Chinese traditional medicine for a long time is due to the fact that unknown components included in the naturally originated yellow coloring matter develop various medicinal effects in addition to the anti-oxidant action of curcumin or tetrahydrocurcumin. Considering polyphenol included in red wine, lycopene included in a red coloring matter of tomato, carthamine included in a red coloring matter of red safflower and the like, which are, for example, known as a naturally originated anti-oxidant substances, are included in a coloring matter, even when the anti-oxidant substance is specified to be curcumin or tetrahydrocurcumin, various medicinal effects proved by curcumin included in the yellow coloring matter are considered to be first developed by interacting the anti-oxidant substance with the other components included in the naturally originated coloring matter.

SUMMARY OF THE INVENTION

It is, therefore, important to considerably enhance the anti-oxidant effect of curcumin included in the curcuma and to provide a naturally originated safe anti-oxidant substance capable of utilizing without damaging other components included in the yellow coloring matter of the curcuma.

The inventor has developed an invention based on the following idea from a viewpoint of "human also rusts". That is, conversations that body odor was hated are heard in a crowded electric car, work place or the like, which is not merely solved by a language of old fogy or the like. Because, such an odor is an oxidation odor produced due to the lowering of anti-oxidation ability (SDO active action) with age, which is not a problem in the odor but is one of oxidation phenomena in any place of a body like a rust in iron or a patination in copper. Oxygen drawn for living changes into an active oxygen due to the lowering of a metabolism, which is an undesirable action of oxygen like oxidation of meat or fish. A visually observed place of such a phenomenon is an aged pattern or a spot. When such an aging phenomenon is carried out in the body, diseases due to the lowering of function or so-called adult diseases are caused, which are serious problems oxidizing any one of heart, liver, gastrointestinal tract, blood vessel, brain and the like in view of the national premium countermeasure. Since funds used to deal with aged diseases such as spot of brain in Alzheimer's disease, which is free in children and youth, and the like becomes remarkably large and oppresses the premium system and aging countermeasure, the inventor has picked up curcumin included in curcuma and having an anti-oxidant property and searched content in accordance with kind of plant, natural growing conditions and the like from east Asia to Mexico and noticed a raw material having a highest concentration of curcumin and discovered that a strength thereof can be increased up to 45%, and as a result, the invention has been accomplished. Even in the textile industry, many companies try their utmost to develop deodorized underwear, but only a masking action is attained and there is no bodily solution. The body is oxidized due to the lowering of function with age. Although an oxygen-removing material may be used for a package of foods, the invention is to effectively utilized for fighting a breathing body against "rust".

The invention was developed under the above circumstances and is to provide a novel anti-oxidant reducing substance having an excellent anti-oxidant effect, which can safely be ingested as well as a method of producing an anti-oxidant reducing substance which can safely and stably supply product.

According to the first aspect of the invention, there is the provision of an anti-oxidant reducing substance to be reduced with hydrogen isolated from calcium ion using water as a solvent, characterized in that calcium powder obtained by adding a calcium ionized water to calcium powder and drying is added to a powdery curcuma. In the invention, curcumin in the curcuma is reduced by taking the anti-oxidant substance with water to develop a higher anti-oxidant action.

In a preferred embodiment, a ratio of calcium ion powder added to the powdery curcuma is 10–0.2%. The powdery curcuma and calcium ion powder are adjusted to a particle size of not less than 100 mesh.

In the other preferred embodiment, a starting material for calcium ion is powder of shell of oyster or powder of shell of abalone. The powder of shell of oyster (BOREI) is calcium powder obtained from the shell of the oyster, while powder of shell of abalone is calcium powder obtained from a shell of an abalone.

According to a second aspect of the invention, there is the provision of a method of producing an anti-oxidant reducing substance to be reduced with hydrogen isolated from calcium ion using water as a solvent, characterized in that calcium ionized water obtained by charging calcium into an electrolysis vessel of water is sprayed onto calcium powder and dried to form calcium ion powder and then the calcium ion powder is added to powdery curcuma. In this case, the calcium ion powder is used as a catalyst and water is used as a solvent to form free hydrogen, which reduces curcumin of the curcuma to enhance the anti-oxidant effect.

In a preferred embodiment, powder shell of oyster or powder of shell of abalone is charged into the electrolysis vessel of water to produce the calcium ionized water.

BRIEF DESCRIPTION OF THE DRAWING

The invention will be described with reference to the accompanying drawing, wherein:

FIG. 1 is a diagrammatic view of an electrolysis vessel of water used in the invention.

DETAILED DESCRIPTION OF THE INVENTION

The anti-oxidant substance according to the invention uses curcuma as an essential component. As the curcuma, there can be used a commercially available curcuma used as a Chinese traditional medicine, spices or the like. And also, a higher anti-oxidant effect is particularly obtained by using a southern produced curcuma having a high curcumin content.

The anti-oxidant substance according to the invention is obtained by adding calcium ion power to the powdery curcuma, which is ingested together with water. These powders are adjusted to a particle size of not less than 100 mesh in order to facilitate the ingestion.

The calcium ion powder is obtained by adding calcium powder with ionic water and drying it. The calcium ion powder is added at a ratio of 10–0.2% to curcuma. When the addition ratio of the calcium ion powder is more than 10%, fishy smelling (animal odor) becomes strong and hence troubles are caused in use. While, when it is less than 0.2%, color change to red is not observed and the effect of the invention can not expected. As the calcium powder, commercially available calcium or calcium made from shell, bone or other substance may be used, but the use of powder of shell of oyster or powder of shell of abalone is particularly preferable. The powder of shell of oyster (BOREI) is calcium powder obtained from the shell of the oyster, while powder of shell of abalone is calcium powder obtained from a shell of an abalone. These calcium powders contain a slight amount of silicate in addition to calcium carbonate, so that they are suitable for the extraction of free hydrogen. Especially, the powder of shell of oyster is very easily available because the oyster shells disposed up to the present can be reutilized as an effective resource.

The production method according to the invention will be described below. Firstly, there are provided calcium powder pulverized to about 100 mesh and calcium granules having a particle size larger than that of the calcium powder. As the calcium granule is used granules formed at a step of forming calcium powder. Moreover, calcium other than the granule may be used. Then, the calcium granules P are charged into an electrolysis vessel 1 of water to prepare calcium ionized water Q (see FIG. 1). In this case, the calcium granules P are placed inside a cathode in the electrolysis vessel I to produce the calcium ionized water Q at the side of the cathode. When powder of shell of oyster or powder of shell of abalone is used as a starting material of calcium powder to be charged into the electrolysis vessel, silicate included in such a starting material can promote the generation of free hydrogen in the electrolysis. Other calcium material and another substance containing silicate can be charged together into the electrolysis vessel.

Furthermore, calcium ionized water is sprayed onto calcium powder having a particle size of about 100 mesh and dried to obtain calcium ion powder. The calcium ion powder is added to curcuma at a ratio of 10–0.2%. Moreover, the addition ratio is 2% in the following example for analysis.

TABLE 1

| Specimen | Item of analytical test | Result | Note | Analytical method |
| --- | --- | --- | --- | --- |
| Domestica curcumin | Super oxide eliminating ability | 200 unit/g | 1 | Electron spin resonance (ESR) method |
| Reduction -type domestica curcumin | Super oxide eliminating ability | 290 unit/g | 1 | Electron spin resonance (ESR) method |

Note 1. unit defined by J. M. McCord and I. Fridovich [as eliminating ability corresponding to J. Biol. Chem., 244, 6049(1969)]

Table 1 shows analytical results through an electron spin resonance (ESR) process by a foundation, Japan Food Analysis Center, wherein the anti-oxidant substance according to the invention has an ability of eliminating active oxygen. The data show that the elimination ability of the starting material (domestica curcumin) prior to the treatment according to the invention is 200 unit/g, while the elimination ability of the anti-oxidant substance according to the invention (reduction type domestica curcumin) is 290 unit/g, from which it is clear that the anti-oxidant effect is considerably improved by the anti-oxidant substance according to the invention.

TABLE 2

| Object to be | Temperature | PH | ORP | Remarks |
|---|---|---|---|---|
| A | H$_2$O 200 cc | 14 | 6.64 | +208 | tap water |
| B | 5 g of curcumin added to 200 cc of item A | 14 | 6.33 | +405 | water:curcumin = 200 cc:5 g |
| C | 0.1 g of calcium ion powder added to 200 cc of item A | 14 | 10.82 | +68 | water:calcium ion powder = 200 cc:0.1 g |
| D | 5 g of curcumin and 0.1 g of calcium ion powder added to 200 cc item A | 14 | 7.67 | +131 | curcumin:calcium ion powder = 100:2 |
| E | Microhydrine powder | 14 | 8.65 | −96 | as powdery hydrogen in test of curcumin for color change into red |

*ORP = OXIDATION REDUCTION POTENTIAL
*PH = POWER HYDROGEN

Table 2 shows results measured on oxidation-reduction potential (ORP) every component in the anti-oxidant substance according to the invention. As the numerical value of ORP becomes low, the reduction becomes promoted. As a result, ORP of the anti-oxidant substance according to the invention (specimen D) is +131, which is "reduction" as compared with a case that ORP value of a tap water (specimen A) is +208 and ORP value of usual curcumin (specimen B) is +405.

And also, it has been confirmed that the anti-oxidant substance according to the invention changes into a red color when water is added as a solvent. Such a color change into red is considered to be common of a natural product containing an anti-oxidant substance such as polyphenol included in a red wine, lycopene included in the red coloring matter of a tomato, carthamin included in a red coloring matter of a red safflower and the like. Therefore, it is considered that a part of curcumin is reduced into a high anti-oxidant substance such as tetrahydrocurcumin and also any component included in the red coloring matter is included into the anti-oxidant substance according to the invention.

According to the invention, there can be provided a novel anti-oxidant reducing substance having an excellent anti-oxidant effect and capable of be safely ingested.

Further, curcumin in the curcuma is reduced by free hydrogen generated from calcium ion powder when curcuma, powder of shell of oyster and powder of shell of abalone are used as starting material and water is used as a solvent, so that the production is very safe as compared with the conventional production method conducting the reduction with a hydrogen gas. And also, the stable supply can be always realized without depending upon environmental conditions such as temperature, humidity, pH value and the like as in the production method using the mycelium and culture of the microorganism.

Moreover, the novel anti-oxidant substance effectively utilizes a naturally originated coloring matter of the curcuma is produced different from the conventional production method extracting and synthesizing only tetrahydrocurcumin, so that there can be expected the effect of promoting various medicinal effects such as control of liver disorder, increase of immune force in the body and the like in addition to the high anti-oxidant effect.

As mentioned above, according to the invention, a very safe anti-oxidant substance can stably be provided and supplied from easily available natural products, so that the invention develops various useful effects in industry.

What is claimed is:

1. An anti-oxidant substance comprising:
   a combination of a dried calcium ion powder and a powdery curcuma, the dried powder obtained by combining a calcium ionized water with a calcium powder and drying, wherein the substance is capable of reducing curcumin in the curcuma with hydrogen ions by combination of the substance with water.

2. The anti-oxidant substance of claim 1, wherein the dried powder is present in an amount of 10–0.2% of the amount of the powdery curcuma by weight.

3. The anti-oxidant substance of claim 1, wherein the dried powder and the powdery curcuma have particle sizes of not less than 100 mesh.

4. The anti-oxidant substance of claim 1, wherein a starting material for the dried powder comprises powder of shell of oyster or powder of shell of abalone.

5. The anti-oxidant substance of claim 4, wherein a starting material for the dried powder comprises a silicate.

6. The anti-oxidant substance of claim 1, wherein the calcium ionized water and the calcium powder are combined by spraying the calcium ionized water onto the calcium powder.

7. The anti-oxidant substance of claim 6, wherein the calcium ionized water is obtained by charging calcium into an electrolysis vessel.

8. The anti-oxidant substance of claim 7, wherein the calcium charged in the electrolysis vessel comprises granules larger in size than the calcium powder.

9. The anti-oxidant substance of claim 1, wherein the substance comprises a yellow color and turns red upon combination with water.

10. The anti-oxidant substance of claim 1, comprising an oxidation-reduction potential of about +131 .

11. A method of producing an anti-oxidant substance comprising:
    charging calcium into an electrolysis vessel to obtain calcium ionized water;
    spraying the ionized water onto a calcium powder and drying to form a dried calcium ion powder; and
    combining the dried powder with a powdery curcuma.

12. The method of claim 11, wherein the dried powder is present in an amount of 10–0.2% of the amount of the powdery curcuma by weight.

13. The method of claim 11, wherein the dried powder and the powdery curcuma have particle sizes of not less than 100 mesh.

14. The method of claim 11, wherein a starting material for the calcium charged into the electrolysis vessel comprises powder of shell of oyster or powder of shell of abalone.

15. The method of claim 11, wherein a starting material for the calcium charged into the electrolysis vessel comprises a silicate.

* * * * *